United States Patent [19]

Haffer et al.

[11] Patent Number: 5,329,009

[45] Date of Patent: Jul. 12, 1994

[54] SELECTIVE PHENYLATION OF 5-HYDROXY-β-CARBOLINE DERIVATIVES

[75] Inventors: Gregor Haffer; Helmut Börner; Klaus Nickisch; Julius Deutsch, all of Berlin, Fed. Rep. of Germany

[73] Assignee: Schering Aktiengesellschaft, Berlin and Bergkamen, Fed. Rep. of Germany

[21] Appl. No.: 854,827

[22] Filed: Mar. 19, 1992

[30] Foreign Application Priority Data

Mar. 19, 1991 [DE] Fed. Rep. of Germany ....... 4109342

[51] Int. Cl.[5] ........................................... C07D 471/04
[52] U.S. Cl. ...................................................... 546/86

[58] Field of Search ............................................ 546/86

[56] References Cited

U.S. PATENT DOCUMENTS 4,894,377  1/1990  Seidelmann et al. ............... 514/292
4,945,090  7/1990  Schmiechen et al. ............ 514/232.8

Primary Examiner—Marianne M. Cintins
Assistant Examiner—Phyllis G. Spivack
Attorney, Agent, or Firm—Millen, White, Zelano & Branigan

[57] ABSTRACT

Disclosed is chemoselective phenylation of 5-hydroxy-β-carbolines in the presence of weak bases while adding water.

10 Claims, No Drawings

SELECTIVE PHENYLATION OF 5-HYDROXY-β-CARBOLINE DERIVATIVES

SUMMARY OF THE INVENTION

The invention relates to the process for the production of optionally substituted 5-phenoxy-β-carbolines.

Because of their affinity to the benzodiazepine receptors, β-carbolines are used as pharmaceutical agents with psychotropic effect. Of the known β-carbolines, 5-phenoxy-β-carbolines, which are described, for example, in EP-A-130 140 (corresponding to U.S. Pat. No. 4,894,377) and EP-A-234 173 (corresponding to U.S. Pat. No. 4,945,090), show very good effectiveness, so that the industrial-scale synthesis of these compounds is of great interest.

The one-stage process described in EP-A-234 173 appears best of all suitable for the synthesis of 5-phenoxy-β-carbolines. In this process, fluorobenzene derivatives in a basic medium in dipolar aprotic solvents are optionally reacted also in the presence of phase transfer catalysts. But with the alkali hydroxides and alkali carbonates mentioned as bases, the phenylation is possible only with a 70% yield, since under the reaction conditions, substitution of the β-carboline also takes place in 9-position. This diphenylated by-product, which is obtained in a 30% yield, can be removed from the reaction product only by extremely expensive chromatographic separating operations, and then has to be discarded.

It was therefore desirable to develop a process which on an industrial scale makes possible the synthesis of the active ingredients of the pharmaceutical agents in good yields.

It has been found, surprisingly, that by selecting a suitable base and by adding water to the aprotic solvent, the formation of the O,N-diarylated product is almost completely suppressed and the desired product is obtained in an over 90% yield by simple crystallization.

This result is also especially surprising to one skilled in the art, because the hydrolysis of fluoronitrobenzene under alkaline conditions at room temperature and even more so at an elevated temperature is generally known, and would be expected.

The invention relates to the process for the production of compounds of formula I

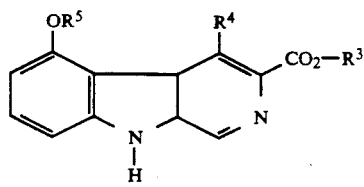

(I)

in which
R³ is $C_{1-6}$ alkyl,
R⁴ is hydrogen, $C_{1-4}$ alkyl, $C_{1-4}$ alkoxy-$C_{1-2}$ alkyl and
R⁵ is phenyl optionally substituted 1-2 times, characterized in that a compound of formula II

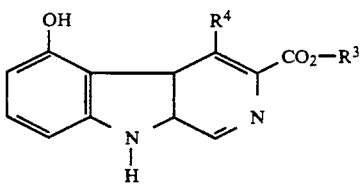

(II)

in which
R³ and R⁴ have the above-named meaning, is reacted with a compound of formula III R⁵-F., in which R⁵ has the above-named meaning, in the presence of a base and while adding water.

The reaction is performed at elevated temperatures, of about 80°-110° C. in aprotic dipolar solvents, such as dimethylformamide, dimethylacetamide, dimethylsulfoxide, hexamethylphosphoric acid triamide, N-methylpyrrolidinone and/or tetramethylurea.

The reaction is generally completed after 5-9 hours.

As bases for the reaction according to the invention, in particular, weak bases are preferred. These bases make possible the formation of the phenolate anion, such as, for example, metal bicarbonates or lithium hydroxide.

According to the invention, water is added in about 10-20 percent by volume relative to the solvent used.

Alkyl is to be understood to mean a straight-chained or branched alkyl radical each, such as, for example, methyl, ethyl, n-propyl, isopropyl, n-butyl, isobutyl, sec-butyl, tert-butyl, pentyl, isopentyl, hexyl, i.a., preferably with up to 4 carbon atoms.

The phenyl radical can be substituted in any position, 1-2 times, and the 2- and/or 4-position is preferred.

As a substituent of the phenyl radical, in particular the NO₂ group is preferred, and the following groups also are preferred as second substituents: halogens, such as fluorine, chlorine, bromine and iodine, cyano, trifluoromethyl, $C_{1-4}$ alkoxy and $C_{1-4}$ alkyl.

The nitrophenoxy-β-carboline derivatives produced according to the invention can be further processed analogously to the methods described in EP-A-234 173.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application P 41 09 342.9, filed Mar. 19, 1991, and disclosing that water is added in about 10-20% by volume relative to the solvent used, are hereby incorporated by reference.

EXAMPLES

EXAMPLE 1

A solution of 15.7 g of 5-hydroxy-4-methoxymethyl-β-carboline isopropyl ester in 223 ml of DMF and 34.5 ml of water is mixed with 13.2 of potassium bicarbonate and 7 ml of 4-fluoronitrobenzene and heated for 6 hours to 90° C. Then, it is concentrated by evaporation in a vacuum at about a 70° C. bath temperature to about 40 ml, the oily residue is diluted with 100 ml of toluene, 200 ml of water is added, it is stirred for 30 more minutes and brought to crystallization in an ice bath. Then the precipitated crystals are suctioned off, rewashed twice with 40 ml of ice-cold toluene and twice with 40 ml of water and dried. 19.65 g of 4-methoxymethyl-5-(4-nitrophenoxy)-β-carboline-3-carboxylic acid isopropyl ester of melting point 217°–219° C. is obtained.

EXAMPLE 2

3.0 g of 5-hydroxy-4-methoxymethyl-β-carboline-3-carboxylic acid ethyl ester in 45 ml of dimethylformamide is dissolved, it is mixed with 6.75 ml of water, 2.22 g of sodium bicarbonate and 1.86 g of 4-fluoronitrobenzene are added in succession and heated for 7 hours to 95° C. After corresponding working up, as indicated in Example 1, 3.98 g of 4-methoxymethyl-5-(4-nitrophenoxy)-β-carboline-3-carboxylic acid ethyl ester of melting point 231°–232° C. is obtained.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the production of a compound of formula I

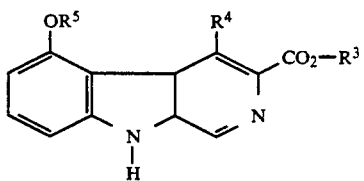

in which
$R^3$ is $C_{1-6}$ alkyl,
$R^4$ is hydrogen, $C_{1-4}$ alkyl or $C_{1-4}$ alkoxy-$C_{1-2}$-alkyl and
$R^5$ is a phenyl radical optionally substituted 1-2 times, said process comprising reacting a compound of formula II (II)

in which
$R^3$ and $R^4$ have the above-named meaning, with a compound of formula III, $R^5$—F     (III)

in which $R^5$ is defined as above, in the presence of a base, the improvement wherein water is added during the reaction in an amount sufficient to suppress the formation of undesired byproducts.

2. A process according to claim 1, wherein the reaction is performed in the presence of a weak base.

3. A process according to claim 1, wherein the reaction is performed in the presence of an aprotic, dipolar solvent.

4. A process according to claim 3, wherein water is added in an amount of about 10–20% by volume, relative to the solvent used.

5. A process according to claim 2, wherein the base is an alkali metal bicarbonate or lithium hydroxide.

6. A process according to claim 1, wherein $R^5$ is phenyl substituted by $NO_2$, halogen, cyano, trifluoromethyl, $C_{1-4}$-alkoxy or $C_{1-4}$alkyl.

7. A process according to claim 1, wherein $R^5$ is substituted in the 2-position, the 4-position, or in both the 2- and 4-positions.

8. A process according to claim 6, wherein $R^5$ is substituted in the 2-position, the 4-position, or in both the 2- and 4-positions.

9. A process according to claim 6, wherein $R^5$ is phenyl substituted by $NO_2$.

10. A process according to claim 1, wherein the formation of O,N-diarylated products is suppressed so that the compound of formula I is produced in over 90% yield.

* * * * *